United States Patent [19]

Cook et al.

[11] 4,200,746

[45] Apr. 29, 1980

[54] CEPHALOSPORINS

[75] Inventors: Martin C. Cook, Liverpool; Gordon I. Gregory, Chalfont St. Peter; Janice Bradshaw, Harrow, all of England

[73] Assignee: Glaxo Laboratories, Ltd., Greenford, England

[21] Appl. No.: 888,242

[22] Filed: Mar. 20, 1978

Related U.S. Application Data

[63] Continuation of Ser. No. 642,300, Dec. 19, 1975, abandoned.

[30] Foreign Application Priority Data

Dec. 20, 1974 [GB] United Kingdom ............... 55213/74

[51] Int. Cl.$^2$ ............................................. C07D 501/20
[52] U.S. Cl. ....................................... 544/25; 424/246
[58] Field of Search .......................................... 544/25

[56] References Cited

U.S. PATENT DOCUMENTS

| | | | |
|---|---|---|---|
| 4,024,133 | 5/1977 | Cook et al. | 544/25 |
| 4,024,134 | 5/1977 | Gregson et al. | 544/25 |
| 4,079,178 | 3/1978 | Cook et al. | 544/25 |

FOREIGN PATENT DOCUMENTS 2204060 8/1972 Fed. Rep. of Germany.
2223375 11/1972 Fed. Rep. of Germany.

*Primary Examiner*—Nicholas S. Rizzo
*Attorney, Agent, or Firm*—Bacon & Thomas

[57] ABSTRACT

Cephalosporin antibiotics in which the 7$\beta$-acylamido group has the formula

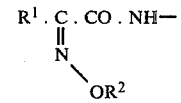

(where $R^1$ is furyl or thienyl and $R^2$ is $C_{1-4}$ alkyl, $C_{3-7}$ cycloalkyl, furylmethyl or thienylmethyl) and in which the 3-position substituent is a pyridiniummethyl group wherein the pyridine ring is optionally substituted by carbamoyl, carboxy, carboxymethyl, sulpho or methyl exhibit high antibacterial activity against a broad range of gram-positive and gram-negative organisms, coupled with particularly high stability to $\beta$-lactamases produced by various gram-negative organisms and good stability in vivo, particularly to esterases.

16 Claims, No Drawings

CEPHALOSPORINS

This is a continuation, of application Ser. No. 642,300, filed Dec. 19, 1975, now abandoned.

This invention is concerned with improvements in or relating to antibiotics of the cephalosporin series.

The cephalosporin compounds in this specification are named with reference to "cepham" after *J.Amer.-Chem.Soc.* 1962, 84, 3400, the term "cephem" referring to the basic cepham structure with one double bond.

Many cephalosporin compounds possessing a degree of antibacterial activity are known in the art, these compounds possessing $\Delta^3$ unsaturation and ordinarily being substituted at the 3-position by a methyl or substituted methyl group and at the 7β-position by an acylamido group. It is now well recognised that the antibiotic properties of a particular ceph-3-em-4-carboxylic acid are predominantly controlled by the nature of both the 7β-acylamido group thereof and the 3-position substituent which the compound carries; considerable research has been undertaken to find combinations of such groups which will yield antibiotics with particular properties.

Cephalosporin antibiotics are widely used in the treatment of diseases caused by pathogenic bacteria in human beings and animals, for example in the treatment of diseases caused by bacteria which are resistant to other antibiotics such as penicillin compounds and in the treatment of penicillin-sensitive patients. In many applications it is desirable to employ a cephalosporin antibiotic which exhibits activity against both gram positive and gram negative microorganisms, and a significant amount of research has been directed to the development of improved board spectrum cephalosporin antibiotics.

The practical utility of a significant number of known commercial and experimental cephalosporin antibiotics is limited by their relatively high susceptibility to the β-lactamases which are produced by many bacteria. A desirable property of a broad spectrum cephalosporin antibiotic is therefore that it should exhibit substantial resistance to β-lactamases, including those produced by gram negative microorganisms.

A further difficulty with many cephalosporin antibiotics intended for therapeutic applications is that they are subject to degradation in vivo. Thus a significant number of known cephalosporin antibiotics have been found to suffer the disadvantage that following administration they are deactivated, often rapidly, by enzymes (e.g. esterases) present in the body.

As a result of extensive studies of numerous cephalosporin compounds we have now found a class of cephalosporin antibiotics having a particular combination of 7β-acylamido group and 3-position substituent which endows the compounds with good broad spectrum activity coupled with the above described desiderata of high β-lactamase stability and good stability in vivo.

According to one aspect of the present invention, therefore, there are provided antibiotic compounds of the formula

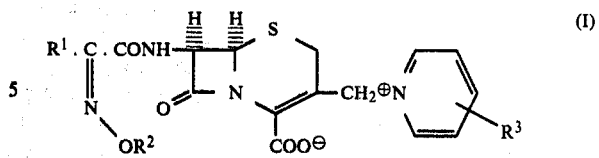

(where $R^1$ represents a furyl or thienyl group; $R^2$ represents a $C_1$–$C_4$ alkyl group, especially methyl, a $C_3$–$C_7$ cycloalkyl group, a furylmethyl group or a thienylmethyl group; and $R^3$ represents a hydrogen atom or a carbamoyl, carboxy, carboxymethyl, sulpho or methyl group) and non-toxic derivatives thereof, the compounds being syn isomers or existing as mixtures of syn and anti isomers containing at least 90% of the syn isomer. Most preferably the compounds are the syn isomers essentially free from the corresponding anti isomers.

The compounds of the invention are defined as having the syn isomeric form as regards the configuration of the group $OR^2$ with respect to the carboxamido group. In this specification the syn configuration is structurally denoted thus:

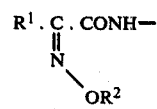

The syn configuration is assigned on the basis of the work of Ahmad and Spenser as reported in *Can.J.-Chem.* 1961, 39, 1340.

The term "non-toxic" as applied to derivatives of the compounds of formula I means those derivatives which are physiologically acceptable in the dosage at which they are administered. Such derivatives may include, for example, salts, biologically acceptable esters, 1-oxides and solvates (especially hydrates) of the compounds (I).

Salts which may be formed from the compounds of formula I where $R^3$ comprises an acidic function include inorganic base salts such as alkali metal (e.g. sodium and potassium) and alkaline earth metal (e.g. calcium) salts, and organic base (e.g. procaine, phenylethylbenzylamine, dibenzylethylenediamine, ethanolamine, diethanolamine, triethanolamine and N-methylglucamine) salts. The salts may also comprise resinates formed with, for example, a polystyrene resin or cross-linked polystyrene divinylbenzene copolymer resin containing amino or quaternary amino groups.

Where $R^1$ in formula I is a furyl group it may be fur-2-yl or fur-3-yl and when it is a thienyl group it may be thien-2-yl or thien-3-yl.

As indicated above, the group $R^2$ in formula I may represent an alkyl group containing 1–4 carbon atoms (e.g. a methyl, ethyl or t-butyl group) or a cycloalkyl group containing 3–7 carbon atoms (e.g. a cyclopentyl group). Alternatively it may be a furylmethyl or thienylmethyl group.

The compounds of the invention, as indicated above, possess a particularly valuable combination of properties, exhibiting high antibacterial activity against a broad range of gram-positive and gram-negative organisms. The breadth of the activity spectrum is enhanced by the particularly high stability of the compounds to β-lactamases produced by various gram-negative organisms. The compounds show the advantageous property of good stability in vivo, particularly to esterases.

The properties possessed by the compounds according to the invention render them useful in the treatment of a variety of diseases caused by pathogenic bacteria in human beings and animals.

An important compound according to the invention is (6R,7R)-7-[2-(fur-2-yl)-2-methoxyiminoacetamido]-3-pyridiniummethylceph-3-em-4-carboxylate (syn isomer), which has the formula

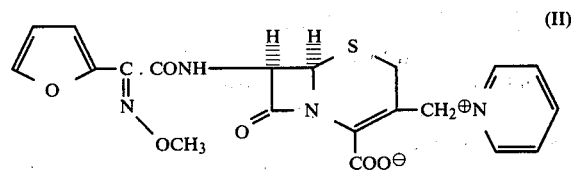

This compound is active against a wide range of gram-positive and gram-negative microorganisms, e.g. *Staphylococci* (including *Staphylococcus aureus*), *Haemophilus influenzae*, *Escherichia coli*, *Pseudomonas*, *Proteus* and *Enterobacter* species.

Other important compounds according to the invention, by virtue of their high antibacterial activity, particularly against gram-negative organisms, and good water solubility are (6R,7R)-7-[2-(fur-2-yl)-2-methoxyiminoacetamido]-3-(2-methylpyridiniummethyl)ceph-3-em-4-carboxylate (syn isomer) and (6R,7R)-3-(3-carboxymethylpyridiniummethyl)-7-[2-(fur-2-yl)-2-methoxyiminoacetamido]ceph-3-em-4-carboxylate (syn isomer) and its salts, e.g. the sodium salt.

According to a further aspect of the invention we provide a process for the preparation of an antibiotic compound of formula I (as hereinbefore defined) and non-toxic derivatives (e.g. salts, esters, 1-oxides and solvates) thereof which comprises either (A) reacting a pyridine compound of the formula

(wherein $R^3$ has the above-defined meanings) with a compound of the formula

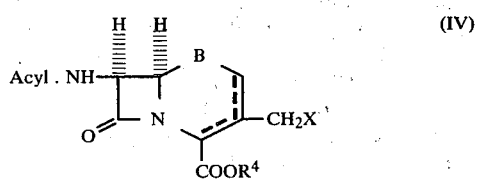

[wherein Acyl is the group

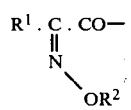

(in which $R^1$ and $R^2$ have the above defined meanings) or a precursor therefor, e.g. a group of formula

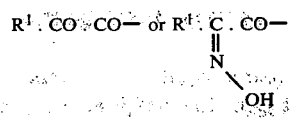

(where $R^1$ has the above-defined meaning); B is $>$S or $>$S→O; $R^4$ is hydrogen or a carboxyl blocking group, e.g. the residue of an ester-forming aliphatic or araliphatic alcohol or an ester-forming phenol, silanol or stannanol or a symmetrical or mixed anhydride group derived from an appropriate acid; the dotted line bridging the 2-, 3- and 4-positions of the molecule indicates that the compound may be a ceph-2-em or a ceph-3-em compound and X is a substituent which is displaceable by a pyridine compound of formula III above], or (B) condensing a compound of formula

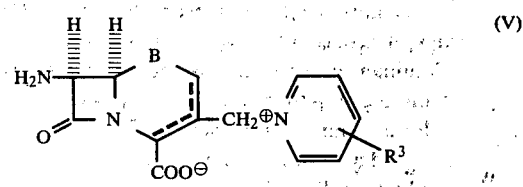

(wherein $R^3$, B and the dotted line have the above-defined meanings) or an acid addition salt (formed with, for example, a mineral acid such as hydrochloric, hydrobromic, sulphuric, nitric or phosphoric acid or an organic acid such as methane sulphonic or toluene p-sulphonic acid) or an N-silyl derivative thereof, or a corresponding compound possessing a blocked carboxy group at the 4-position, with an acylating agent corresponding to an acid of formula

(wherein $R^1$ and $R^2$ have the above-defined meanings) or with an acylating agent corresponding to an acid which is a precursor for the acid (VI), e.g. an acid of formula

or

(where $R^1$ has the above-defined meaning); whereafter, if necessary and/or desired in each instance, any of the following reactions (C), in any appropriate sequence are carried out:

(i) conversion of a precursor for the desired

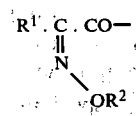

group into that said group, (ii) conversion of a $\Delta^2$ isomer into the desired $\Delta^3$ isomer, (iii) removal of any carboxyl blocking groups, and (iv) reduction of a cephalosporin sulphoxide product to yield the corresponding sulphide; and finally (D) recovering the desired compound of formula I, if necessary after separation of syn and anti isomers and if desired after conversion of the compound to a non-toxic derivative thereof.

Non-toxic derivatives of the compounds of formula I may be formed in any convenient way, for example according to methods well known in the art. Thus, for example, base salts of compounds (I) wherein $R^3$ contains an acidic function may be formed by reaction with an appropriate base or salt; where insoluble salts of such compounds (I) are required, e.g. for use in depot preparations, these may be formed in conventional manner. 1-Oxides may be formed by, for example, treatment of the corresponding cephalosporin sulphide with an appropriate oxidising agent, for example with a peracid such as metaperiodic acid, peracetic acid, monoperphthalic acid or m-chloroperbenzoic acid, or with t-butyl hypochlorite, conveniently in the presence of a weak base such as pyridine.

There are now described particular operating procedures for the various reaction steps which may be employed in the preparation of compounds of formula I.

(A) Nucleophilic Displacement

The pyridine compound of formula III may act as a nucleophile to displace a wide variety of substituents X from the exocyclic 3-methylene group of the cephalosporin of formula IV. To some extent the facility of the displacement is related to the pKa of the acid HX from which the substituent is derived. Thus atoms or groups X derived from strong acids tend, in general, to be more easily displaced than atoms or groups derived from weaker acids. For example, the reaction may conveniently by effected on 3-halomethyl cephalosporins, i.e. compounds (IV) wherein X is chlorine, bromine or iodine. The facility of the displacement is also related, to some extent, to the precise character of the substituent $R^3$ in the compound of formula III.

Nucleophilic displacement reactions may conveniently be carried out on those compounds of formula IV wherein the substituent X belongs to one or other of four principal classes. The classes are characterised by whether it is a halogen, oxygen, nitrogen or sulphur atom in the substituent X that is bonded to the exocyclic methylene group in the compound of formula IV. These classes of X substituent are discussed below.

Halogens

Compounds of formula IV in which X is chlorine, bromine or iodine are advantageous materials for use in the nucleophilic displacement reaction with the pyridine compound of formula III. In the case of reactions carried out on compounds of formula IV in which $R^4$ is a carboxyl blocking group the 3-pyridiniummethyl product will be formed as the corresponding halide salt.

Oxygen bonded groups

Compounds of formula IV possessing X substituents of this class include compounds wherein X is the residue of acetic acid; in this case the compound (IV) may have been obtained in a small number of steps from cephalosporin C. This class also includes substituents X which are the residue of an acetic acid derivative having at least one electron-withdrawing group on the α-carbon atom, e.g. X groups of formula $$-O.CO.C(R^5)_3$$

where each $R^5$ is selected from halogen (e.g. chlorine), $C_{1-4}$ alkoxy (e.g. methoxy), $C_{1-4}$ alkylthio (e.g. methylthio) and cyano, with the additional possibility that one or two of $R^5$ may be hydrogen. Such groups, and other useful oxygen-bonded X groups, for example nuclear-substituted benzoyloxy groups in which the nuclear substituent or substituents are selected from $C_{1-4}$ alkyl (e.g. methyl), halogen (e.g. chlorine or bromine), nitro, $C_{1-4}$ haloalkyl (e.g. trifluoromethyl), carbamoyl, cyano and esterified carboxyl (e.g. $C_{2-5}$ alkoxycarbonyl such as methoxycarbonyl), are described in greater detail in British Patent Specification No. 1,241,657, the contents of which are herein incorporated by reference.

Displacement reactions on compounds (IV) possessing X substituents of this class may be facilitated by the presence in the reaction medium of iodide or thiocyanate ions. Reactions of this type are described in more detail in British Patent Specification Nos. 1,132,621 and 1,171,603, the contents of which are incorporated herein by reference.

The substituent X may also be derived from formic acid or a haloformic acid such as chloroformic acid.

Nitrogen bonded groups

This class of groups includes the group $-N=C=S$.

Sulphur bonded groups

This class of groups includes groups of formula $$-SY$$

where Y is a group $R^5.C(:Z)-$ or $R^5.SO_2-$ in which Z is oxygen or sulphur and $R^5$ is an aliphatic, aryl, araliphatic, heterocyclic or heterocyclic substituted aliphatic group.

Displacement reactions on compounds (IV) possessing X substituents of this class may be facilitated by the presence in the reaction medium of a salt of mercury, silver or gold. The salt should be ionizable in water and capable of complexing with the group $-SY$. Reactions of this type are described in more detail in British Pat. No. 1,101,424, the contents of which are incorporated herein by reference.

Reaction Conditions for the Displacement of X by the Pyridine Compound (III)

The displacement of X by the pyridine compound (III) may conveniently be effected by maintaining the reactants in solution or suspension at a moderate temperature, e.g. from $-40°$ to $+120°$ C.

The reaction is advantageously effected using from one to ten molar equivalents of the pyridine compound. The pH value of the reaction solution under aqueous conditions is advantageously maintained in the range 5–8. When working under non-aqueous conditions it is preferred that polar solvents be employed; the reaction medium should be neither extremely basic nor extremely acidic.

Organic solvents such as dioxan, ethyl acetate, formamide, N,N-dimethylformamide or acetone may be employed. The organic solvents may be used in the presence or absence of water. In certain cases the pyridine compound itself may be the solvent. Other suitable organic solvents are described in more detail in British Pat. No. 1,326,531.

The reaction product may be separated from the reaction mixture, which may contain, for example, unchanged cephalosporin and other substances, by a variety of processes including recrystallisation, ionophoresis, paper chromatography and use of ion-exchangers (for example by chromatography on ion-exchange resins).

(B) Acylation

Compounds of formula I may conveniently be prepared by condensing a compound of formula V with an acylating agent comprising an acid halide, particularly an acid chloride or bromide, corresponding to the acid (VI). Such acylation may be effected at temperatures of from −50° to +50° C., preferably −20° to +30° C. The acylation is conveniently effected in aqueous media.

Acylation with an acid halide may be effected in the presence of an acid binding agent (e.g. a tertiary amine such as triethylamine or dimethylaniline, an inorganic base such as calcium carbonate or sodium bicarbonate, or an oxirane, preferably a lower-1,2-alkylene oxide such as ethylene oxide or propylene oxide) which serves to bind hydrogen halide liberated in the acylation reaction.

Acylation may also be effected with other amide-forming derivatives of the acid (IV) such as, for example, a symmetrical anhydride or a mixed anhydride, e.g. with pivalic acid or formed with a haloformate such as a lower alkyl haloformate. The mixed or symmetrical anhydrides may be generated in situ; thus, for example, a mixed anhydride may be generated using N-ethoxycarbonyl-2-ethoxy-1,2-dihydroquinoline. Mixed anhydrides may also be formed with phosphorus acids (for example phosphoric or phosphorous acids), sulphuric acid or aliphatic or aromatic sulphonic acids (for example p-toluenesulphonic acid).

As indicated above, analogues of compounds (V) having a blocked carboxy group at the 4-position may also be employed as starting materials; it will be appreciated that such compounds will have an anion, for example a halide ion, associated with the 3-pyridiniummethyl group.

(C) Subsequent Reactions

Where a cephalosporin compound having a precursor acyl group of formula

(where $R^1$ has the above-defined meaning) at the 7β-position is prepared, the acyl group may be converted to the desired group by reacting the compound with an etherified hydroxylamine compound of formula $$R^2O.NH_2 \qquad (IX)$$

(where $R^2$ has the above-defined meaning). Separation of isomers to give the required syn isomer may be effected before or after removal of any blocking group from the 4-carboxy group and may be effected by, for example, crystallisation or chromatography.

Where a cephalosporin compound having a precursor acyl group of formula

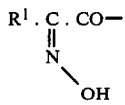

(where $R^1$ has the above-defined meaning) at the 7β-position is prepared, the acyl group may be converted to the desired group by etherification to introduce a group $R^2$ as defined above. Suitable etherifying agents include appropriate halides, sulphates, sulphonates (e.g. tosylates), diazoalkanes, alkyl fluorosulphonates and trialkyloxonium tetrafluoroborates. Etherifications using diazo compounds, fluorosulphonates and tetrafluoroborates may require assistance, e.g. with a Lewis acid such as $BF_3$.

Any blocking group substituting the 4-carboxy group of the cephalosporin starting materials in the processes described above is desirably a group which may readily be split off at a later stage of a reaction sequence, and advantageously is a group containing 1–20 carbon atoms. Suitable blocked carboxyl groups are well known in the art, a list of representative groups being included in our British Patent No. 1,399,086. Preferred blocked carboxyl groups include aryl lower (e.g. $C_{1-4}$) alkoxycarbonyl groups such as p-methoxybenzyloxycarbonyl, p-nitrobenzyloxycarbonyl oxycarbonyl and diphenylmethoxycarbonyl; and lower haloalkoxycarbonyl groups such as 2,2,2-trichloroethoxycarbonyl. The carboxyl blocking group may subsequently be removed by any of the appropriate methods disclosed in the literature; thus, for example, acid or base catalysed hydrolysis is applicable in many cases, as are enzymically-catalysed hydrolyses.

One useful technique for removing an esterifying group such as a diphenylmethyl group from the 4-carboxy group comprises treating the cephalosporin 4-ester with trifluoroacetic acid, conveniently in the presence of anisole. It has been observed, however, that when, in the preparation of compounds of the present invention, an ester of a compound (I) is obtained as a halide salt, for example as a result of using a starting material (IV) where X is halogen and $R^4$ is an esterifying group in step (A) of the process defined above, subsequent de-esterification of this salt by treatment with trifluoroacetic acid tends to promote isomerisation of the oxyimino moiety in the 7β-acylamido side chain; such isomerisation is clearly undesirable if a product containing at least 90% of the syn isomer is to be obtained without the need for a subsequent isomer separation stage.

It has been observed by our co-worker Dr. Christopher M. D. Beels, however, that this tendency to isomerisation may be substantially lessened if the 3-pyridiniummethyl cephalosporin ester halide (which may be in the form of a 1-oxide) is converted to a 3-pyridinium methyl cephalosporin ester salt of a non-hydrohalic acid (e.g. trifluoroacetic, acetic, formic, sulphuric, nitric or phosphoric acid) prior to deesterification. Conversion of the halide salt into a non-hydrohalic acid salt is conveniently effected by means of anion exchange. This may be brought about by, for example, use of a suitable anion exchange resin, for example in the trifluoroacetate form. Where an anion exchange resin is employed, the 3-pyridiniummethyl cephalosporin ester halide may be run through a column of the resin prior to deesterification. It may be advantageous to employ an inert organic solvent system (i.e., one which does not have a harmful effect on the resin) to ensure adequate solubility for the cephalosporin compound; organic solvent system which may be used include lower alkanols such as ethanol, ketones such as acetone, and nitriles such as acetonitrile.

Where at the end of a given preparative sequence a sulphoxide analogue of a compound of formula I is obtained, conversion to the corresponding sulphide may, for example, be effected by reduction of the corresponding acyloxysulphonium or alkyloxysulphonium salt prepared in situ by, for example, reaction with acetyl chloride in the case of an acetoxysulphonium salt, reduction being effected by, for example, sodium dithionite or by iodide ion (as in a solution of potassium iodide in a water miscible solvent such as acetic acid, tetrahydrofuran, dioxan, dimethylformamide or dimethylacetamide). The reaction may be effected at a temperature of $-20°$ to $+50°$ C.

Where the reaction product is a ceph-2-em-4-carboxylic ester the desired ceph-3-em compound may be obtained by treatment of the former with a base.

The antibiotic compounds according to the invention may be formulated for administration in any convenient way, by analogy with other antibiotics and the invention therefore includes within its scope a pharmaceutical composition comprising a compound of formula I or a non-toxic derivative (e.g. a salt, biologically acceptable ester, 1-oxide or solvate) thereof in a form adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers with added preservative. The compositions may take such forms as suspensions, solutions and emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

For veterinary medicine the compositions may, for example, be formulated as intramammary preparations in either long acting or quick-release bases.

In general the compositions may contain from 0.1% upwards, e.g. 0.1–99%, preferably from 10–60% of the active material, depending on the method of administration. Where the compositions comprise dosage units, each unit will preferably contain 50–1500 mg of the active ingredient. The dosage as employed for adult human treatment will preferably range from 500–5000 mg per day, depending on the route and frequency of administration.

The compounds according to the invention may be administered in combination with other compatible therapeutic agents such as antibiotics, for example penicillins, other cephalosporins or tetracyclines.

The following novel compounds, of value as intermediates in the preparation of antibiotic compounds of general formula I, comprise a further feature of the invention:

diphenylmethyl (1S,6R,7R)-3-bromomethyl-7-[2-(fur-2-yl)-2-methoxyiminoacetamido]ceph-3-em-4-carboxylate 1-oxide (syn isomer);

diphenylmethyl (1S,6R,7R)-3-(3-carbamoylpyridiniummethyl)-7-[2-(fur-2-yl)-2-methoxyiminoacetamido]-ceph-3-em-4-carboxylate bromide 1-oxide (syn isomer);

diphenylmethyl (6R,7R)-3-(3-carbamoylpyridiniummethyl)-7-[2-(fur-2-yl)-2-methoxyiminoacetamido]ceph-3-em-4-carboxylate bromide (syn isomer);

diphenylmethyl (6R,7R)-3-(3-carbamoylpyridiniummethyl)-7-[2-(fur-2-yl)-2-methoxyiminoacetamido]-ceph-3-em-4-carboxylate trifluoroacetate (syn isomer);

diphenylmethyl (1S,6R,7R)-3-(4-carbamoylpyridiniummethyl)-7-[2-(fur-2-yl)-2-methoxyiminoacetamido]-ceph-3-em-4-carboxylate bromide 1-oxide (syn isomer);

diphenylmethyl (6R,7R)-3-(4-carbamoylpyridiniummethyl)-7-[2-(fur-2-yl)-2-methoxyiminoacetamido]-ceph-3-em-4-carboxylate bromide (syn isomer);

diphenylmethyl (6R,7R)-3-(4-carbamoylpyridiniummethyl)-7-[2-(fur-2-yl)-2-methoxyiminoacetamido]-ceph-3-em-4-carboxylate trifluoroacetate (syn isomer);

diphenylmethyl (1S,6R,7R)-3-(3-carbamoylpyridiniummethyl)-7-[2-(fur-2-yl)-2-methoxyiminoacetamido]-ceph-3-em-4-carboxylate trifluoroacetate 1-oxide (syn isomer); and diphenylmethyl (1S,6R,7R)-3-(4-carbamoylpyridiniummethyl)-7-[2-(fur-2-yl)-2-methoxyiminoacetamido]ceph-3-em-4-carboxylate trifluoroacetate 1-oxide (syn isomer).

The following Examples illustrate the invention. All temperatures are in ° C. Amberlite LA2 resin is a liquid secondary amine ion exchanger. XAD 2 is a synthetic insoluble cross-linked polystyrene polymer. Deacidite FF and Dowex-1 resins are quaternary ammonium ion exchange resins. IRC 50 resin is a carboxylic acid cation exchanger.

EXAMPLE 1

(6R,7R)-7-[2-(Fur-2-yl)-2-methoxyiminoacetamido]-3-pyridiniummethyl-ceph-3-em-4-carboxylate (syn isomer)

A solution of (6R,7R)-3-acetoxymethyl-7-[2-(fur-2-yl)-2-methoxyiminoacetamido]ceph-3-em-4-carboxylic acid (syn isomer) (4.89 g) in water (50 ml) and pyridine (4.0 ml) was heated at 80° for 70 minutes. The cooled reaction mixture was evaporated under reduced pressure to small bulk to remove excess pyridine. The mixture was diluted with water to about 70 ml and washed successively with methylene chloride (2×30 ml), a solution of Amberlite LA2 resin (5 ml) in methylene chloride (50 ml), and methylene chloride (3×30 ml). The washings were themselves washed with water (30 ml), and the aqueous phases were combined and evaporated to a yellow glass (2.17 g) under reduced pressure at <40°. The crude product when warmed with dimethylacetamide (10 ml) started to crystallise and the process was completed by dilution with acetone (10 ml) and refrigeration for 16 hours, producing the title compound solvate (1.68 g), $\lambda_{max}$ (pH 6 buffer) 260 nm ($\epsilon$ 18,800); $\nu_{max}$ (Nujol) 1770 ($\beta$-lactam), 1678 and 1550 (CONH) and 1620 cm$^{-1}$ (CO$_2^-$); $\tau$(D$_2$O; 100 MHz) 0.98, 1.39, 1.87 (pyridine protons), 2.30, 3.15, 3.38(furyl protons, syn isomer), 4.15(d, J4 Hz; 7-H), 4.72(d, J4 Hz; 6-H), 6.04(s; CH$_3$), 6.33, 6.80 (dd, J 18 Hz; 2-H$_2$), 4.38, 4.63(dd, J14 Hz; CH$_2$N$^+$), 6.96, 7.10, 7.93 (dimethylacetamide, 0.7 mole) and 7.78 (acetone, 0.15 mole).

EXAMPLE 2

(6R,7R)-7-[2-(Fur-2-yl)-2-methoxyiminoacetamido]-3-(3-sulphopyridiniummethyl)ceph-3-em-4-carboxylate, sodium salt(syn isomer)

A suspension of pyridine-3-sulphonic acid (3.2 g) in water (ca. 25 ml) was treated with sodium hydroxide solution to pH 6. A small amount of amorphous material was filtered off and the filtrate evaporated to dryness under reduced pressure. Sodium iodide (20 g) and water (7.5 ml) were added to the residual solid and the mixture was stirred and heated to 80°. Sodium (6R,7R)-3-acetoxymethyl-7-[2-(fur-2-yl)-2-methoxyiminoacetamido]ceph-3-em-4-carboxylate (syn isomer) (4.45 g) was added to the hot solution over 10 minutes and the mixture was heated for a further 50 minutes at 80°. The cooled reaction mixture was diluted with water to ca 125 ml, methylisobutylketone (2 drops) was added and the mixture stirred during acidification to ca pH 1 with 2 N hydrochloric acid. A little Kieselguhr was added, the mixture was filtered and the filtrate was acidified to pH 1 with a little 2 N hydrochloric acid. The solution was extracted with ethyl acetate ($3 \times 100$ ml), and the extracts were washed with water (ca. 40 ml). The combined aqueous phases were adjusted to pH 6 with sodium hydroxide solution and then evaporated under reduced pressure at $<40°$ to 50 ml. A column of XAD-2 resin (500 g:$4 \times 80$ cm) was prepared and washed with water (ca. 1 liter). The reaction solution was introduced to the column and eluted with water, the fractions being collected automatically. The progress of the separation was followed by U.V. spectrometry. The inorganic salts and excess nucleophile were eluted first and then fractions containing the product were collected, combined and evaporated to small volume under reduced pressure at $<40°$ and finally freeze dried. The amorphous product was finally dried over phosphorus pentoxide to give the title compound (2.05 g), $[\alpha]_D = +53°$ (c 1, $H_2O$); $\lambda_{max}$ (pH 6 buffer) 267 nm ($\epsilon$ 19,700); $\nu_{max}$ (Nujol) 1760 ($\beta$-lactam), 1670 and 1540 (CONH), 1610 ($CO_2^-$), 1040 and 1220 cm$^{-1}$ ($SO_3^-$); $\tau(D_2O$; 100 MHz) 0.61, 0.88, 1.15 and 1.79 (pyridinium protons), 2.35, 3.17 and 3.42(furyl protons, syn isomer), 4.14(d, J 4 Hz; 7-H), 4.72(d, J 4 Hz; 6-H), 4.31 and 4.62(2d, J14 Hz; $CH_2^+N$), 6.03(s; $CH_3$) and 6.29 and 6.76(2d, J18 Hz; 2-$H_2$).

EXAMPLE 3

(6R,7R)-3-(3-Carboxypyridiniummethyl)-7-[2-(fur-2-yl)-2-methoxyiminoacetamido]ceph-3-em-4-carboxylate, sodium salt (syn-isomer)

The reaction of nicotinic acid (2.46 g) with sodium (6R,7R)-3-acetoxymethyl-7-[2-(fur-2-yl)-2-methoxyimino acetamido]ceph-3-em-4-carboxylate (syn isomer) (4.45 g), in a similar manner to that used in Example 2, gave the title compound (1.51 g), $[\alpha]_D + 69°$ (c 1, $H_2O$); $\lambda_{max}$ (pH 6 buffer) 270 nm ($\epsilon$ 17,600); $\tau(D_2O$; 100 MHz) 0.69, 0.96, 1.11 and 1.88 (pyridinium protons), 2.32, 3.16 and 3.39(furyl protons, syn isomer) 4.12(d, J4 Hz; 7-H), 4.68(d, J4 Hz; 6-H), 4.32 and 4.60(2d, J14 Hz; -$CH_2N^+$), 6.01(s; $CH_3$), and 6.29 and 6.76 (2d, J18 Hz; 2-$H_2$).

EXAMPLE 4

(6R,7R)-3-(3-Carboxymethylpyridiniummethyl)-7-[2-(fur-2-yl)-2-methoxyiminoacetamido]ceph-3-em-4-carboxylate, sodium salt (syn isomer)

The reaction of pyrid-3-ylacetic acid (2.74 g) with sodium (6R,7R)-3-acetoxymethyl-7-[2-(fur-2-yl)-2-methoxyiminoacetamido]ceph-3-em-4-carboxylate (syn isomer) (4.45 g), in a similar way to that described in Example 2, gave the title compound (0.91 g), $[\alpha]_D + 76°$ (c 1, $H_2O$); $\lambda_{max}$(pH 6 buffer) 270 nm ($\epsilon$ 20,000); $\tau(D_2O$; 100 MHz) 1.20, 1.59 and 2.02(pyridinium protons), 2.37, 3.19, 3.41 (furyl protons, syn isomer), 4.12(d, J 4 Hz; 7-H), 4.76(d, J 4 Hz; 6-H), 4.46 and 4.70(2d, J14 Hz; $CH_2N^+$), 6.05(s; $CH_3$), 6.24(s; $CH_2CO_2^-$), 6.38 and 6.82(2d, J18 Hz; 2-$H_2$).

EXAMPLE 5

(6R,7R)-3-(2-Carboxypyridiniummethyl)-7-[2-(fur-2-yl)-2-methoxyiminoacetamido]ceph-3-em-4-carboxylate, sodium salt (syn-isomer)

The reaction of 2-carboxypyridine (2.46 g) with sodium (6R,7R)-3-acetoxymethyl-7-[2-(fur-2-yl)-2-methoxyiminoacetamido]ceph-3-em-4-carboxylate (4.45 g), in a similar way to that described in Example 2, gave the title compound (0.21 g), $\lambda_{max}$(pH 6 buffer) 275 nm ($\epsilon$ 19,900); $\tau(D_2O$; 100 MHz) 1.12, 1.46, 1.96, 2.01 (pyridinium protons) 2.34, 3.16, 3.40(furyl protons, syn isomer), 4.16(d, J 5 Hz; 7-H), 4.41 (s; $CH_2N^+$), 4.76(d, J5 Hz; 6-H), 6.03(s; $CH_3$), 6.43 and 6.79 (2d, J18 Hz; 2-$H_2$).

EXAMPLE 6

(6R,7R)-7-[2-(Fur-2-yl)-2-methoxyiminoacetamido]-3-(2-methylpyridiniummethyl)ceph-3-em-4-carboxylate (syn isomer)

Pyrid-2-ylacetic acid hydrochloride (3.47 g) was dissolved in water (ca. 25 ml) and treated with sodium hydroxide solution to pH 7. The solution was evaporated to near dryness under reduced pressure and reacted with sodium (6R,7R)-3-acetoxymethyl-7-[2-(fur-2-yl)-2-methoxyimino acetamido]ceph-3-em-4-carboxylate (4.45 g) in a similar way to that described in Example 2, to give the title compound (0.68 g), $\lambda_{max}$ (pH 6 buffer) 271 nm ($\epsilon$ 19,400); $\nu_{max}$ (Nujol) 1768 ($\beta$-lactam), 1658 and 1526 (CONH) and 1600 ($CO_2^-$); $\tau(D_2O$; 100 MHz) 1.29, 1.63, 2.12 and 2.16(pyridinium protons), 2.33, 3.18 and 3.41 (furyl protons, syn isomer), 4.16(d, J5 Hz; 7-H), 4.76(d, J5 Hz; 6-H), 4.45 and 4.70(2d, J 15 Hz; $CH_2N^+$), 6.03 (s; $OCH_3$), 7.18(s; $CH_3$) and 6.50 and 6.80(2d, J18 Hz; 2-$H_2$).

EXAMPLE 7

(a) Diphenylmethyl (1S,6R,7R)-3-Bromomethyl-7-[2-(fur-2-yl)-2-methoxyiminoacetamido]ceph-3-em-4-carboxylate 1-Oxide (syn-isomer)

To a solution of phosphorus pentachloride (3.7 g) in dried dichloromethane (40 ml) at $-10°$ was added N,N-dimethylacetamide (8.25 ml.) and then, slowly, syn-2-(fur-2-yl)-2-methoxyiminoacetic acid (3.00 g), the temperature being kept at approximately $-10°$. The resulting solution was stirred for 15 minutes, then ice (9 g) was added and the temperature of the solution allowed to rise to 0° over 10 minutes. The organic layer was added to a stirred suspension of diphenylmethyl (1S,6R,7R)-7-amino-3-bromomethylceph-3-em-4-carboxylate 1-oxide, hydrobromide (7.34 g) in dried dichloromethane (100 ml) and propylene oxide (10 ml) at 0°. The reaction mixture was stirred for 45 minutes, during which time it was allowed to warm up to room temperature. To the resulting suspension was added methanol (60 ml) and this mixture was stirred for 10 minutes and then filtered. The white solid was washed with methanol and dried to give the title ester as a white microcrystalline powder (5.26 g, 64%), m.p. 186°-190° (decomp.); $[\alpha]_D$ −4.5° (c 1.0, DMSO); $\lambda_{max}$ (EtOH) 281 nm ($\epsilon$ 22,600). IR and NMR spectroscopy confirmed the structure as that of the title ester.

Concentration of the mother liquor afforded further white solid, which was filtered off, washed with methanol and dried to give more title ester as a white solid (2.371 g, 28.6%).

(b)
(6R,7R)-3-(3-Carbamoylpyridiniummethyl)-7-[2-(fur-2-yl)-2-methoxyiminoacetamido]ceph-3-em-4-carboxylate (syn isomer)

Diphenylmethyl (1S,6R,7R)-3-bromomethyl-7-[2-(fur-2-yl)-2-methoxyiminoacetamido]ceph-3-em-4-carboxylate 1-oxide (syn isomer) (610 mg) suspended in N,N-dimethylformamide (2 ml) and chloroform (1 ml) was stirred with nicotinamide (490 mg) for 30 minutes. The yellow solution was partitioned between chloroform (10 ml) and water (10 ml) containing 2 N-hydrochloric acid (2 ml). The organic layer was separated, the aqueous layer was extracted with chloroform (5 ml) and the combined chloroform layers were dried and evaporated. The resulting oil was triturated with ethyl acetate (20 ml) to give a white solid which was collected, washed with ethyl acetate and dried to give diphenylmethyl (1S,6R,7R)-3-(3-carbamoylpyridiniummethyl)-7-[2-(fur-2-yl)-2-methoxyiminoacetamido]-ceph-3-em-4-carboxylate bromide 1-oxide (syn-isomer) as a white powder (580 mg, 76%), m.p. 153°-155° (decomp.); $[\alpha]_D$+4.4° (c 1.3, DMSO); $\lambda_{max}$ (EtOH) 274 nm ($\epsilon$ 27,700); the structure of this product was confirmed by IR and NMR spectroscopy.

The above sulphoxide product (1.5 g) in N,N-dimethylformamide (5 ml) containing potassium iodide (1.29 g) was cooled to −10° and treated with acetyl chloride (0.3 ml). The mixture was stirred at −10° for 45 minutes and then added dropwise to a stirred aqueous solution of sodium metabisulphite (1 g) in water (50 ml) to give a yellow precipitate which was collected, washed with water and dried to give the corresponding sulphide (syn isomer) as a yellow powder (1.33 g), m.p. 140°-145° (decomp.); $[\alpha]_D$+2.3° (c 0.4, DMSO); $\lambda_{max}$ (EtOH) 271.5 nm ($E_{1\ cm}^{1\%}$ 275) and 375.5 nm ($E_{1\ cm}^{1\%}$ 52); the structure of this product was confirmed by IR and NMR spectroscopy.

A solution of the above sulphide product (1.2 g) in a mixture of industrial methylated spirit and dichloromethane (ca. 75 ml total) was evaporated until incipient crystallization. The solution was passed down a column of Deacidite F.F ion exchange resin (15 cm×2.5 cm i.d.) in the trifluoroacetate form and the column was eluted with industrial methylated spirit. Fractions containing ultraviolet light-absorbing material were combined and evaporated to a foam which was triturated with ether. The resulting solid was collected, washed and dried to give diphenylmethyl (6R,7R)-3-(3-carbamoylpyridiniummethyl)-7-[2-(fur-2-yl)-2-methoxyiminoacetamido]ceph-3-em-4-carboxylate trifluoroacetate (syn isomer) (1.11 g, 71% based on the sulphoxide salt), m.p. 125°-133° (decomp.); $[\alpha]_D$ −31.7° (c 0.3, DMSO); $\lambda_{max}$ (EtOH) 269.5 ($\epsilon$ 21,400); the structure of this product was confirmed by IR and NMR spectroscopy.

The above trifluoroacetate salt (0.916 g) was moistened with anisole (1.0 ml), cooled in an ice-bath and treated slowly with trifluoroacetic acid (4 ml) to give a brown solution. After 10 minutes the mixture was evaporated in vacuo to give an oil which was dissolved in ethyl acetate (20 ml) and the solution was evaporated to a brown foam. Trituration with ether gave a brown solid which was collected and washed with ether. The resulting pale solid was extracted with water (100 ml) and the extract washed successively with ethyl acetate and ether then filtered and freeze dried. The white foam was triturated with ether, collected and washed with ether to give the title compound as a white powder (0.54 g, 80%), m.p. 138°-143° (decomp.); $[\alpha]_D$ −50.5° (c 1.0, DMSO); $\lambda_{max}$ (pH 6 phosphate buffer) 266.5 nm ($\epsilon$ 20,400); $\nu_{max}$ (Nujol) 1780 ($\beta$-lactam) and 1670 cm$^{-1}$ ($CO_2H$, CONH, $CONH_2$); $\tau$($d_6$-DMSO) values include 0.22 (d, J8 Hz; CONH), 1.31 and 1.88(2s; $CONH_2$), 2.20 (furyl, $C_{(5)}$-H), 3.33(d, J4 Hz; furyl $C_{(3)}$-H), 3.41(m; furyl $C_{(4)}$-H), 4.16(dd, J5 and 8 Hz; 7-H) and 6.14(s; $OCH_3$). Analysis showed part of this product to be present as the trifluoroacetate (0.67 mole).

EXAMPLE 8

(6R,7R)-3-(4-Carbamoylpyridiniummethyl)-7-[2-(fur-2-yl)-2-methoxyiminoacetamido]ceph-3-em-4-carboxylate (syn isomer)

In a similar manner to that described in Example 7(b), diphenylmethyl (1S,6R,7R)-3-bromomethyl-7-[2-(fur-2-yl)-2-methoxyiminoacetamido]ceph-3-em-4-carboxylate 1-oxide (syn-isomer) (611 mg) was treated with isonicotinamide (488 mg) for 1 hour to give diphenylmethyl (1S,6R,7R)-3-(4-carbamoyl-1-pyridiniummethyl)-7-[2-(fur-2-yl)-2-methoxyiminoacetamido]ceph-3-em-4-carboxylate bromide 1-oxide (syn isomer) (0.63 g, 81%), m.p. 153°-155° (decomp.); $[\alpha]_D$ −18.1° (c 0.16, DMSO); $\lambda_{max}$ (EtOH) 275.5 ($\epsilon$ 23,000) and 375 nm ($\epsilon$ 3,100); $\nu_{max}$ ($CHBr_3$) 1786 ($\beta$-lactam) and 1709 cm$^{-1}$ ($CO_2R$).

The above sulphoxide (1.5 g) was reduced with potassium iodide and acetyl chloride to the corresponding sulphide (syn isomer) isolated as mixed halide salts, $\lambda_{max}$ (EtOH) 267 nm ($E_{1\ cm}^{1\%}$ 220); $\nu_{max}$ (Nujol) 1790 ($\beta$-lactam) and 1720 cm$^{-1}$ ($CO_2R$). Ion exchange chromatography on Deacidite F.F. in the trifluoroacetate form gave diphenylmethyl (6R,7R)-3-(4-carbamoylpyridiniummethyl)-7-[2-(fur-2-yl)-2-methoxyiminoacetamido]ceph-3-em-4-carboxylate trifluoroacetate (syn-isomer) (0.53 g, 34% based on the sulphoxide), m.p. 142°-144° (decomp.); $[\alpha]_D$ −131° (c 0.7, DMSO); $\lambda_{max}$ (EtOH) 267.5 ($\epsilon$ 19,600) and 374 nm ($\epsilon$ 1,100); $\nu_{max}$ ($CHBr_3$) 1792 ($\beta$-lactam) and 1713 cm$^{-1}$ ($CO_2R$).

Deprotection with trifluoroacetic acid in anisole for 10 minutes in an ice bath gave the title compound (0.24 g, 97%), m.p. 140°-144° (decomp.); $[\alpha]_D$ −67° (c 1.0, DMSO); $\lambda_{max}$ (pH6 phosphate buffer) 269.5 nm ($\epsilon$ 23,100); $\nu_{max}$ (Nujol) 1779 ($\beta$-lactam), 1670 and 1535 cm$^{-1}$ (CONH, $CONH_2$); $\tau$ ($d_6$-DMSO) values include 0.24(d, J8 Hz, CONH), 1.25 and 1.74 (2s; $CONH_2$), 4.16(dd, J5 and 8 Hz; 7-H) and 6.13(s; $OCH_3$). Analysis showed this product to be present largely as the trifluoroacetate (0.7 mole).

EXAMPLE 9

(6R,7R)-7-[2-(Fur-2-yl)-2-methoxyiminoacetamido]-3-pyridiniummethylceph-3-em-4-carboxylate (syn-isomer)

A solution of 2-(fur-2-yl)-2-methoxyiminoacetic acid (syn isomer) (0.93 g), triethylamine (0.76 ml) and dimethylformamide (1 drop) in dry methylene chloride (15 ml) was cooled in an ice-bath and treated with oxalyl chloride (0.48 ml). After 1 hour the solvents were removed by evaporation under reduced pressure and the residue was suspended in dry acetone (20 ml).

A solution of (6R,7R)-7-amino-3-pyridiniummethyl-ceph-3-em-4-carboxylate dihydrochloride (1.82 g) in water (50 ml) and acetone (20 ml) was adjusted to pH 5 with a saturated aqueous solution of sodium hydrogen carbonate. The suspension containing the acid chloride was filtered slowly into the stirred solution and the residue was washed with a little acetone. The addition was carried out over ca. 1 hour and the pH of the reaction mixture was maintained at 5 by the simultaneous addition of a solution of sodium hydrogen carbonate in water. The reaction mixture was concentrated at <40° under reduced pressure to removed acetone and then washed successively with a solution of LA2 resin (2×2 ml) in methylene chloride (2×20 ml), methylene chloride (20 ml) and ether (20 ml).

The aqueous solution was then stirred with IRC 50 resin in the hydrogen form (ca. 5 g) for 30 minutes and filtered. The filtrate was washed with methylene chloride and ether and then passed down a column of Dowex 1 resin in the acetate form. The eluate was freeze-dried to give a pale yellow solid (2.02 g). The solid was redissolved in water (50 ml) and chromatographed on a column of Deacidite FF resin in the acetate form. The progress of the separation was monitored by thin layer chromatography on silica(solvent n-propanol:water, 7:3) and fractions containing the product were combined and freeze-dried to give the title compound (0.54 g) with properties similar to those described for the product of Example 1.

EXAMPLE 10

(6R,7R)-7-[2-Furfuryloxyimino-2-(fur-2-yl)acetamido]-3-pyridiniummethylceph-3-em-4-carboxylate (syn isomer)

A solution of (6R,7R)-3-acetoxymethyl-7-[2-furfuryloxyimino-2-(fur-2-yl)acetamido]ceph-3-em-4-carboxylic acid (syn isomer) in water (150 ml) and pyridine (6.0 ml) was stirred and heated at 95° for 10 minutes. The cooled mixture was washed three times with methylene chloride and the clear aqueous layer evaporated briefly under reduced pressure to remove organic solvents. The solution was applied to a column of Deacidite FF resin in the acetate form and eluted with water. The fractions which when spotted on filter paper gave a purple colour with potassium iodoplatinate were combined and freeze dried to give a yellow solid (2.68 g). The solid (1.4 g) in methanol (5 ml) was added dropwise to acetone (300 ml) with vigorous stirring. After 2 hours the white precipitate was collected and dried over phosphorus pentoxide to give the title compound (0.99 g), $\lambda_{max}$ (pH6 buffer) 262.5 and 280 nm ($\epsilon$ 17,100; 16,900); $\nu_{max}$ (Nujol) 1776 ($\beta$-lactam), 1672 and 1540 (CONH) and 1610 cm$^{-1}$ (CO$_2^-$); $\tau$ (d6-DMSO) 0.13 (d, J 8 Hz; NH), 0.54, 1.30, 1.72 (pyridine protons), 2.11, 3.28, 3.34 (furyl protons, syn isomer), 2.31, 3.44, 3.53 (furfuryl protons), 4.19 (dd, J 5 and 8 Hz; 7-H), 4.78 (d, 5 Hz; 6-H), 4.87 (CH$_2$—), 4.24 and 4.57 (dd, J 14 Hz; CH$_2$N$^+$), 6.36 and 6.78 (dd, J 18 Hz; 2-H$_2$).

EXAMPLE 11

(6R,7R)-7L-[2-Furfuryloxyimino-2-(fur-2-yl)acetamido]-3-pyridiniummethylceph-3-em-4-carboxylate (syn isomer)

The reaction of 2-furfuryloxyimino-2-(fur-2-yl)acetyl chloride (syn isomer), prepared from the corresponding acid (0.94 g) by treating the triethylamine salt with oxalyl chloride, with (6R,7R)-7-amino-3-pyridiniummethylceph-3-em-4-carboxylate dihydrochloride (1.092 g), in a similar manner to that described in Example 9, gave the title compound (0.15 g) which was characterised by its NMR spectrum, this resembling that described for the product of Example 10.

EXAMPLE 12

(6R,7R)-7-[2-cyclopentyloxyimino-2-(fur-2-yl)acetamido]-3-pyridiniummethylceph-3-em-4-carboxylate (syn isomer)

The reaction of (6R,7R)-3-acetoxymethyl-7-[2-cyclopentyloxyimino-2-(fur-2-yl)acetamido]ceph-3-em-4-carboxylic acid (syn isomer) (8.3 g) with pyridine (5.5 ml) in water (120 ml), in a similar manner to that described in Example 10, gave a solid (2.71 g). This material (2.0 g) in water (25 ml) was treated with an aqueous solution of perchloric acid (60% w/w) to pH 1.2. The precipitated salt was collected, washed with a little ice-cold water and dried to give a solid (1.7 g). This solid (1.5 g), dissolved in a minimum volume of N,N-dimethylacetamide (ca. 3.0 ml) was treated with triethylamine (0.45 ml), triturated, and refrigerated for 16 hours. The crystals were collected, washed with ice-cold N,N-dimethylacetamide and then with ether to give the title compound (1.23 g). Recrystallisation of a portion of this material (1.0 g) from a mixture of acetone and water (3.0 ml,85:15) gave pure title compound (0.68 g), $\lambda_{max}$ (pH 6 buffer) 260 and 282 nm ($\epsilon$ 18,000; 18,600); $\tau$ (d$_6$-DMSO; 100 MHz) 0.32 (d, J 8 Hz; NH), 0.55, 1.32 and 1.74 (pyridine protons), 2.15 and 3.36 (furyl protons, syn isomer), 4.17 (dd, J 5 and 8 Hz; 7-H), 4.78 (d, J 5 Hz; 6-H), 4.26 and 4.60 (dd, J 14 Hz; CH$_2$N$^+$), 5.28 and 8.0-8.6 (cyclopentyl protons), 6.34 and 6.76 (dd, J 18 Hz; 2-H$_2$).

EXAMPLE 13

(6R,7R)-7-[2-Methoxyimino-2-(thien-2-yl)acetamido]-3-pyridiniummethylceph-3-em-4-carboxylate (syn isomer)

A solution of (6R,7R)-3-acetoxymethyl-7-[2-methoxyimino-2-(thien-2-yl)acetamido]ceph-3-em-4-carboxylic acid (syn isomer) (10.0 g) in water (100 ml) containing pyridine (8 ml) was stirred for 1 hour at 80°. The reaction mixture was cooled and then evaporated to small bulk to remove excess pyridine. The mixture was diluted with water to about 200 ml and insoluble material was filtered off. The filtrate was stored in a refrigerator for several days and more solid was filtered off and discarded. The filtrate was washed successively with methylene chloride (2×60 ml), a solution of Amberlite LA2 resin (10 ml) in methylene chloride (100 ml), and methylene chloride (3×60 ml), and the washes were themselves washed with water (60 ml). The combined aqueous phase was evaporated under reduced pressure at <40° to give a yellow glass (3.6 g). The crude product was dissolved in warm dimethylacetamide (16 ml) and treated dropwise with acetone until no more solid precipitated. On filtration the solid changed to a gum; this was redissolved in water and evaporated to dryness as before to give a dark yellow solid (2.35 g). A column of XAD -2 resin (500 g; 4×80 cm) was prepared and washed with water (ca. 1 liter). The crude product in water (100 ml) containing a little ethanol was introduced to the column and eluted with water and then water containing increasing quantities of ethanol. The progress of the separation was followed by U.V. spectrometry. The fractions eluted with ethanol:water (1:1) were combined and evaporated to small volume under reduced pressure at <40° and finally freeze dried to give the title compound as a white froth (0.25 g), $\lambda_{max}$ (pH6 buffer) 259 nm ($\epsilon$ 16,700); $\nu_{max}$ (Nujol) 1778 ($\beta$-lactam), 1670 and 1550 (CONH) and 1620 cm$^{-1}$ ($CO_2^-$); $\tau$($d_6$-DMSO; 100 MHz) 0.22 (NH), 0.52, 1.40, 1.84 (pyridinium protons), 2.36 and 2.80–3.0 (thienyl protons, syn isomer), 4.27 (7-H), 4.86 (6-H), 4.27 and 4.82 (2d, J14 Hz; $CH_2N^+$), 6.14 (s; $CH_3$) and 6.39 and 6.90 (2d, J18 Hz; 2-$H_2$).

EXAMPLES OF PHARMACEUTICAL COMPOSITIONS

Example A

Dry Powder for Injection in Solution

Sterile (6R,7R)-3-(3-carboxymethylpyridiniummethyl)-7-[2-(fur-2-yl)-2-methoxyiminoacetamido]ceph-3-em-4-carboxylate, sodium salt (syn isomer) is filled into glass vials, the claimed contents of each container being 500 mg and 1.00 g of the cephalosporin compound. Filling is carried out aseptically under a blanket of nitrogen. The vials are closed using rubber discs or plugs held in position by aluminium sealing rings, thereby preventing gaseous exchange or ingress of microorganisms. The product is intended for reconstitution by dissolving in Water for Injections or other suitable sterile vehicle shortly before administration.

Example B

Dry Powder for Injection in Suspension

| Composition per dose (5 ml):- | |
|---|---|
| (6R,7R)-7-[2-(Fur-2-yl-2-methoxyiminoacetamido]-3-pyridiniummethylceph-3-em-4-carboxylate (syn isomer) | 1.00 g |
| Lecithin | 20 mg |
| Sodium carboxymethyl cellulose (low viscosity) | 30 mg |
| Sodium citrate (anhydrous) | 100 mg |

The sodium carboxymethyl cellulose and anhydrous sodium citrate, both as fine powders, are sterilised by being maintained at 160° for 1 hour. The lecithin is dissolved in chloroform and sterilised by membrane filtration; the solution is then triturated aseptically with the sodium citrate. The chloroform is allowed to evaporate and the thus-obtained lecithin-coated sodium citrate is aseptically sieved or milled. The sterile cephalosporin compound is then intimately blended under aseptic conditions with the sterile lecithin-coated sodium citrate and the sterile sodium carboxymethyl cellulose. The resulting blend is aseptically filled into sterile siliconised glass vials. The vials are closed using rubber discs or plugs held in position by aluminium sealing rings, thereby preventing ingress of microorganisms. A fill weight of 1.265 g (10% overage) is used; the product is intended for reconstitution with Water for Injections shortly before administration, to give a final volume of 5.5 ml and an injectible volume of 5.0 ml.

We claim:

1. A compound selected from the group consisting of a cephalosporin antibiotic of the formula

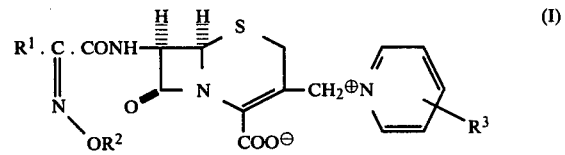

where $R^1$ represents a furyl or thienyl group; $R^2$ represents a $C_1$-$C_4$ alkyl group, a $C_3$-$C_7$ cycloalkyl group, a furylmethyl group or a thienylmethyl group; and $R^3$ represents a hydrogen atom or a carbamoyl, carboxy, carboxymethyl, sulpho or methyl group, and a physiologically acceptable salt, ester or 1-oxide thereof.

2. The compound of claim 1 which is (6R,7R)-7-[2-(fur-2-yl)-2-methoxyiminoacetamido]-3-pyridiniummethylceph-3-em-4-carboxylate (syn isomer).

3. The compound of claim 1 which is (6R,7R)-7-[2-(fur-2-yl)-2-methoxyiminoacetamido]-3-(3-sulphopyridiniummethyl) ceph-3-em-4-carboxylate (syn isomer).

4. The compound of claim 1 which is (6R,7R)-3-(3-carboxypyridiniummethyl)-7-[2-(fur-2-yl)-2-methoxyiminoacetamido]ceph-3-em-4-carboxylate (syn isomer).

5. The compound of claim 1 which is (6R,7R)-3-(3-carboxymethylpyridiniummethyl)-7-[2-(fur-2-yl)-2-methoxyiminoacetamido]ceph-3-em-4-carboxylate (syn isomer).

6. The compound of claim 1 which is (6R,7R)-3-(2-carboxypyridiniummethyl)-7-[2-(fur-2-yl)-2-methoxyiminoacetamido]ceph-3-em-4-carboxylate (syn isomer).

7. The compound of claim 1 which is (6R,7R)-7-[2-(fur-2-yl)-2-methoxyiminoacetamido]-3-(2-methylpyridiniummethyl)ceph-3-em-4-carboxylate (syn isomer).

8. The compound of claim 1 which is (6R,7R)-3-(3-carbamoylpyridiniummethyl)-7-[2-(fur-2-yl)-2-methoxyiminoacetamido]ceph-3-em-4-carboxylate (syn isomer).

9. The compound of claim 1 which is (6R,7R)-3-(4-carbamoylpyridiniummethyl)-7-[2-(fur-2-yl)-2-methoxyiminoacetamido]ceph-3-em-4-carboxylate (syn isomer).

10. The compound of claim 1 which is (6R,7R)-[2-furfuryloxyimino-2-(fur-2-yl)acetamido]-3-pyridiniummethylceph-3-em-4-carboxylate (syn isomer).

11. The compound of claim 1 which is (6R,7R)-7-[2-cyclopentyloxyimino-2-(fur-2-yl)-acetamido]-3-pyridiniummethylceph-3-em-4-carboxylate (syn isomer).

12. The compound of claim 1 which is (6R,7R)-7-[2-methoxyimino-2-(thien-2-yl)acetamido]-3-pyridiniummethylceph-3-em-4-carboxylate (syn isomer).

13. The compound of claim 1 which is (6R,7R)-7-[2-(fur-2-yl)-2-methoxyiminoacetamido]-3-(3-sulphopyridiniummethyl) ceph-3-em-4-carboxylate (syn isomer) sodium salt.

14. The compound of claim 1 which is (6R,7R)-3-(3-carboxypyridiniummethyl)-7-[2-(fur-2-yl)-2-methoxyiminoacetamido]ceph-3-em-4-carboxylate (syn isomer) sodium salt.

15. The compound of claim 1 which is (6R,7R)-3-(3-carboxymethylpyridiniummethyl)-7-[2-(fur-2-yl)-2-methoxyiminoacetamido]ceph-3-em-4-carboxylate (syn isomer) sodium salt.

16. The compound of claim 1 which is (6R,7R)-3-(2-carboxypyridiniummethyl)-7-[2-(fur-2-yl)-2-methoxyiminoacetamido]ceph-3-em-4-carboxylate (syn isomer) sodium salt.

* * * * *